US011471317B1

(12) United States Patent
Spears

(10) Patent No.: US 11,471,317 B1
(45) Date of Patent: Oct. 18, 2022

(54) BED RAIL SAFETY CUFF

(71) Applicant: James M. Spears, Little Rock, AR (US)

(72) Inventor: James M. Spears, Little Rock, AR (US)

( * ) Notice: Subject to any disclaimer, the term of this patent is extended or adjusted under 35 U.S.C. 154(b) by 0 days.

(21) Appl. No.: 17/726,943

(22) Filed: Apr. 22, 2022

(51) Int. Cl.
*A61F 5/37* (2006.01)
*A61G 7/05* (2006.01)

(52) U.S. Cl.
CPC .......... *A61F 5/3761* (2013.01); *A61G 7/0507* (2013.01)

(58) Field of Classification Search
CPC .... A61F 5/3761; A61F 5/3769; A61F 5/3792; A61F 5/3715; A61G 7/0507; A61G 7/0526; A45F 2005/006; A45F 5/02; A45F 5/00; A01K 27/003; G09F 3/005
See application file for complete search history.

(56) References Cited

U.S. PATENT DOCUMENTS

| | | | | |
|---|---|---|---|---|
| 1,596,792 A | * | 8/1926 | Barry | A61F 5/3761 128/878 |
| 2,245,293 A | | 6/1941 | Ogburn | |
| 2,679,842 A | * | 6/1954 | Brill | A61F 5/3769 128/882 |
| 3,027,895 A | * | 4/1962 | Williams | A61F 5/3761 128/878 |
| 3,536,068 A | * | 10/1970 | Stubbs | A61F 5/3761 128/878 |
| 4,422,455 A | * | 12/1983 | Olsen | A61F 5/3761 128/882 |
| 4,628,925 A | | 12/1986 | Witzel | |
| 5,360,019 A | | 11/1994 | Witzel et al. | |
| 5,472,000 A | | 12/1995 | Olsen | |
| 5,546,962 A | | 8/1996 | Power | |
| 5,558,102 A | | 9/1996 | McCarthy | |
| 10,441,453 B2 | * | 10/2019 | Allen | A61F 5/3761 |
| 2017/0165097 A1 | * | 6/2017 | Patmore | A61F 5/3769 |
| 2018/0325717 A1 | * | 11/2018 | Dufek | A61F 5/3776 |

OTHER PUBLICATIONS

Hand cuff Medical Restraint Straps With Magnetic Key,patient fix system,patient reposition strap. Product Listing [online] Copyright © 2014-2021 jayamedical.com [retrieved on Jul. 6, 2021]. Retrieved from the Internet: <URL: https://www.jayamedical.com/sale-2271384-patient-friendly-positioning-medical-restraint-straps-with-magnetic-key.html>.

* cited by examiner

*Primary Examiner* — Camtu T Nguyen
(74) *Attorney, Agent, or Firm* — Cramer Patent & Design, PLLC; Aaron R. Cramer

(57) ABSTRACT

The bed rail safety cuff may comprise a patient cuff, a bed rail clamp, and a restraint. The bed rail safety cuff may be adapted to safely restrain movement of a patient's extremity by coupling the patient's extremity to a bed rail of a hospital bed. As non-limiting examples, restraining a patient may be necessary to prevent the patient from leaving the hospital bed, from pulling out intravenous medication lines, or from damaging medical devices when incoherent. The patient cuff may be adapted to couple to the patient and the bed rail clamp may be coupled to the bed rail. The patient cuff may be coupled to the bed rail clamp by the restraint and the restraint may determine the range of motion possible while restrained. More than one of the safety cuffs may be used to restrain multiple extremities.

15 Claims, 5 Drawing Sheets

BED RAIL SAFETY CUFF

RELATED APPLICATIONS

None.

FIELD OF THE INVENTION

The presently disclosed subject matter is directed to a safety cuff and more specifically to a safety cuff for a hospital bed rail.

BACKGROUND OF THE INVENTION

As anyone who works in law enforcement and the medical field may attest, oftentimes people who need medical attention also require physical constraint. The need for physical constraint may be for the benefit of the individual in custody to prevent self-harm, prevent escape and/or protect those individuals assisting in the care of the restrained individual.

Historically, use of police issue handcuffs or zip-ties were the most often used devices to restrain an individual to a hospital bed. While some facilities that specialize in the treatment of belligerent or dangerous individuals may have more sophisticated means of restraint—such devices are often cumbersome and not readily available. Therefore, a need exists for a restraint device that is safe and cost effective. The development of the bed rail safety cuff fulfills this need.

SUMMARY OF THE INVENTION

The principles of the present invention provide for a bed rail safety cuff that has a patient cuff having a bottom cuff portion and a top cuff portion, a bottom cuff cushion, a strap, a bed rail clamp that includes a bottom clamp portion and a top clamp portion, and a restraint having an extension arm and a lock-in-place tensioner. The restraint couples the patient cuff to the bed rail clamp to determine a range of motion possible while the patient is restrained. The bottom cuff portion includes a bottom cuff shell. The patient cuff is adapted to couple to a patient's extremity with the bottom cuff portion and the top cuff portion on opposing sides of the patient's extremity. The bed rail clamp is adapted to removably couple to the bed rail with the bottom clamp portion and the top clamp portion on opposing sides of the bed rail.

The bottom cuff cushion may be coupled to an inside surface of the bottom cuff shell and may be adapted to cushion the bottom cuff shell between the bottom cuff shell and the patient's extremity for comfort and safety. The bed rail safety cuff may further comprise a bottom cuff tab that may be a projection from the bottom cuff shell oriented at a right angle to the bottom cuff shell and the bottom cuff tab connects the bottom cuff portion to the restraint. The strap may include a hook-and-loop coupler one side of the strap such that the strap folds and couples back upon the strap after passing through a strap retainer located on the top cuff portion. To retain the patient cuff on the patient's extremity, the strap may pass through the strap retainer and the strap may fold back upon the strap. The strap may couple back upon the strap such that the strap creates a loop that passes through the strap retainer. A top cuff cushion may be coupled to an inside surface of the top cuff shell and may be adapted to cushion the top cuff shell between the top cuff shell and the patient's extremity for comfort and safety. A top cuff tab may be a projection from the top cuff shell oriented at a right angle to the top cuff shell. The bottom clamp portion may include a bottom clamp shell that may be a rigid semi-circular armature adapted to be positioned below the bed rail. A bottom clamp inside tab may be a projection from the bottom clamp shell oriented at a right angle to the bottom clamp shell and may be directed towards the patient cuff.

A bottom clamp outside tab may be a projection from the bottom clamp shell oriented at a right angle to the bottom clamp shell and may be directed away from the patient cuff. The bottom clamp outside tab and the bottom clamp inside tab may project in opposite directions from the bottom clamp shell and may connect the bottom clamp portion to the restraint. The bottom clamp outside tab may include one or more outside ball sockets and the bottom clamp inside tab may include one or more inside ball sockets that are a plurality of apertures for coupling the top cuff shell to the bottom cuff shell. The top clamp portion may include a top clamp shell adapted to be positioned above the bed rail. A top clamp inside tab may be a projection from the top clamp shell oriented at a right angle to the top clamp shell and may be directed towards the patient cuff. A top clamp outside tab may be a projection from the top clamp shell oriented at a right angle to the top clamp shell and may be directed away from the patient cuff. The top clamp outside tab and the top clamp inside tab may project in opposite directions from the top clamp shell. The top clamp outside tab may include one or more outside ball studs. The one or more outside ball studs and the one or more inside ball studs may be a plurality of coupling pins for coupling the top cuff shell to the bottom cuff shell.

The top clamp portion and the bottom clamp portion may couple to the bed rail by placing the top clamp portion and the bottom clamp portion on opposing sides of the bed rail and pressing the top clamp portion and the bottom clamp portion together such that the one or more inside ball studs on the top clamp inside tab engage the one or more inside ball sockets on the bottom clamp inside tab and the one or more outside ball studs on the top clamp outside tab engage the one or more outside ball sockets on the bottom clamp outside tab.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
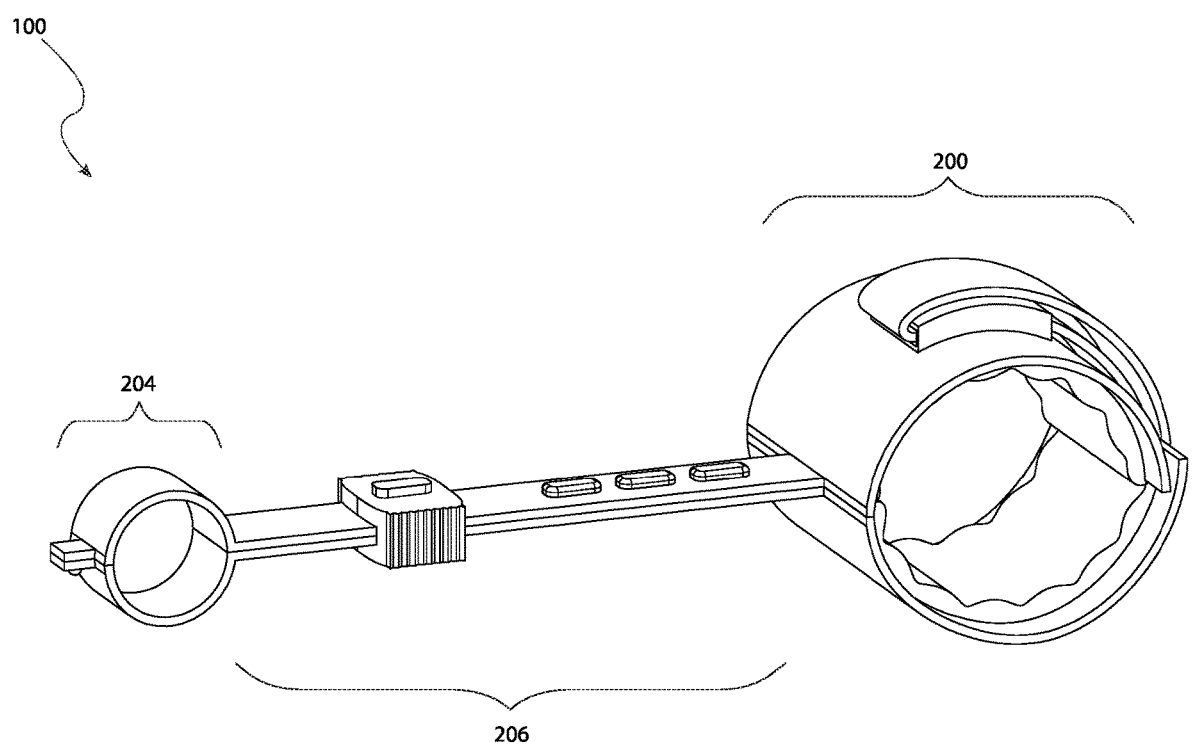
FIG. 1 is a front isometric view of a bed rail safety cuff, according to an embodiment of the present invention.
Figure 2:
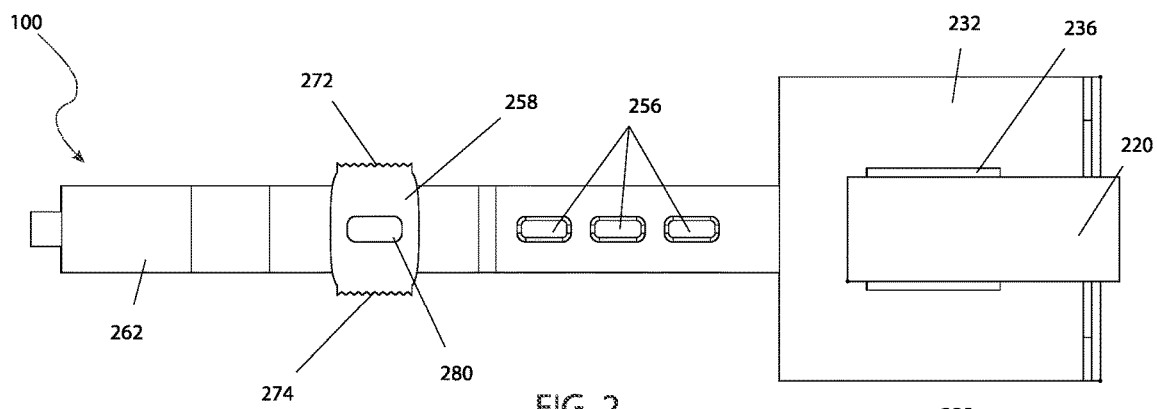
FIG. 2 is a top view of a bed rail safety cuff, according to an embodiment of the present invention.
Figure 3:
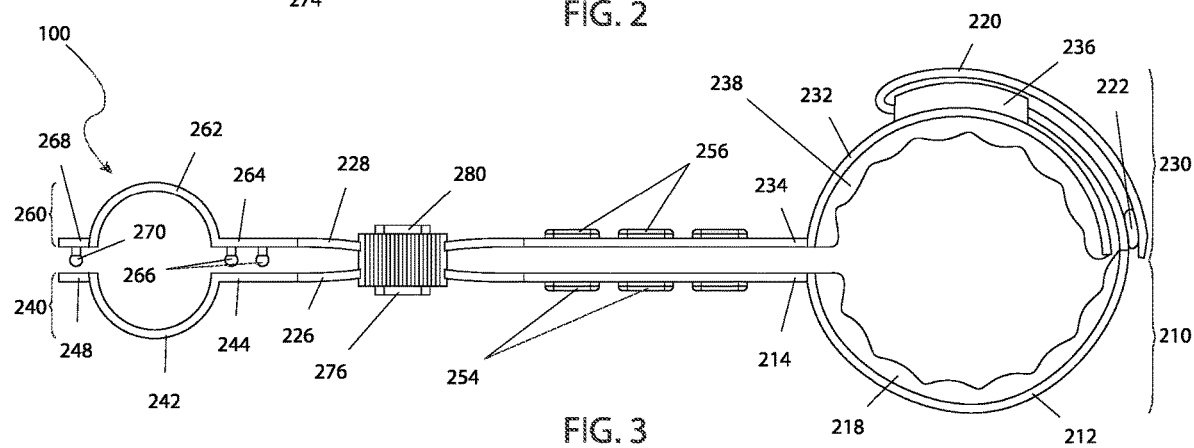
FIG. 3 is a side view of a bed rail safety cuff, according to an embodiment of the present invention.
Figure 4:
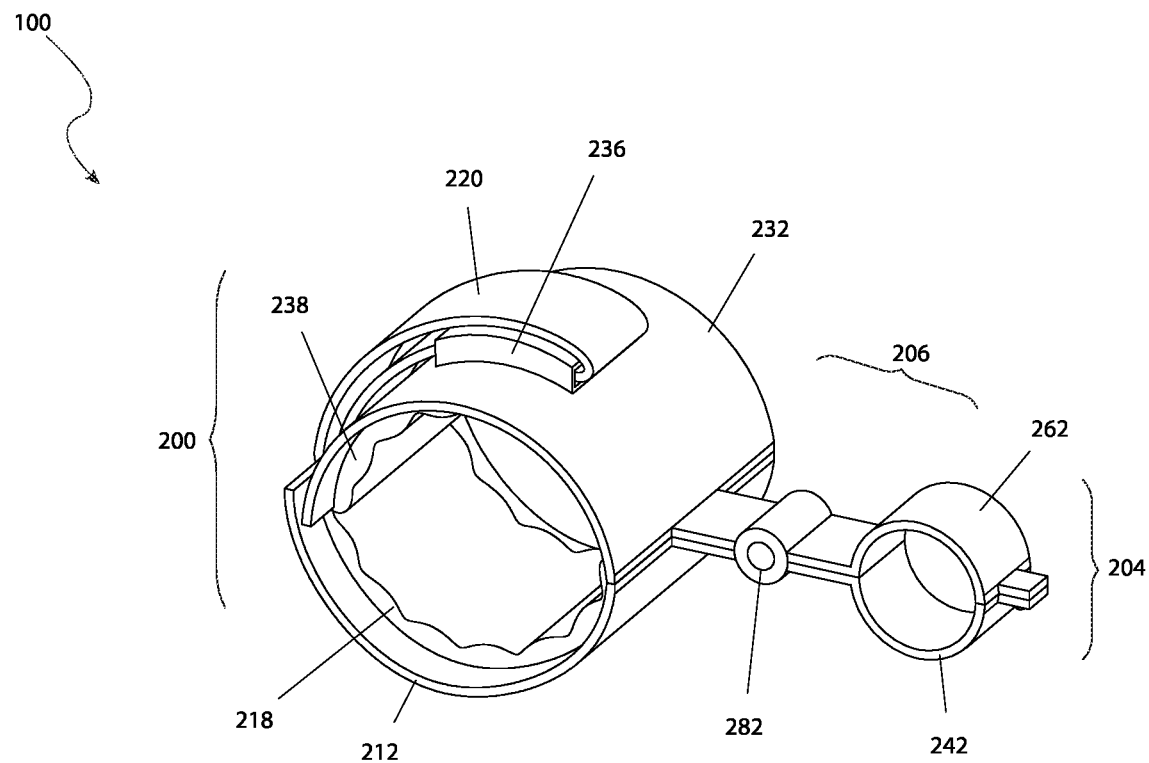
FIG. 4 is a rear isometric view of a bed rail safety cuff, according to a first alternative embodiment of the present invention.
Figure 5:
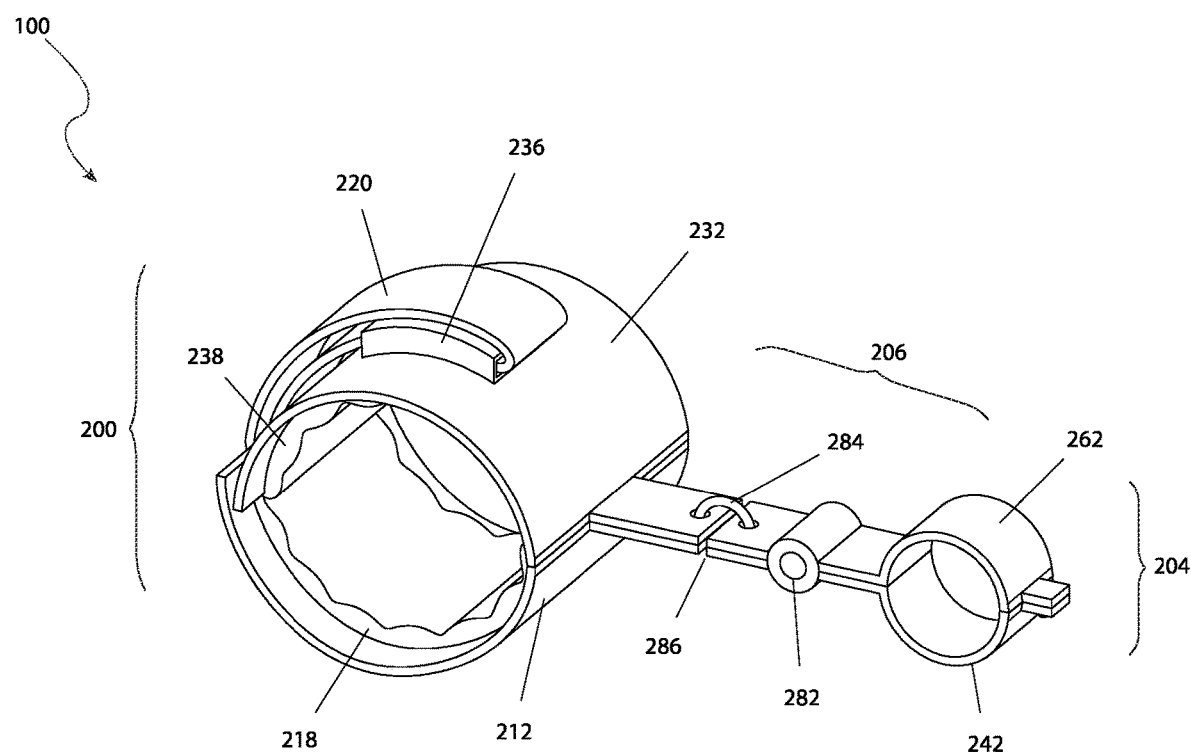
FIG. 5 is a rear isometric view of a bed rail safety cuff, according to a second alternative embodiment of the present invention.
Figure 6:
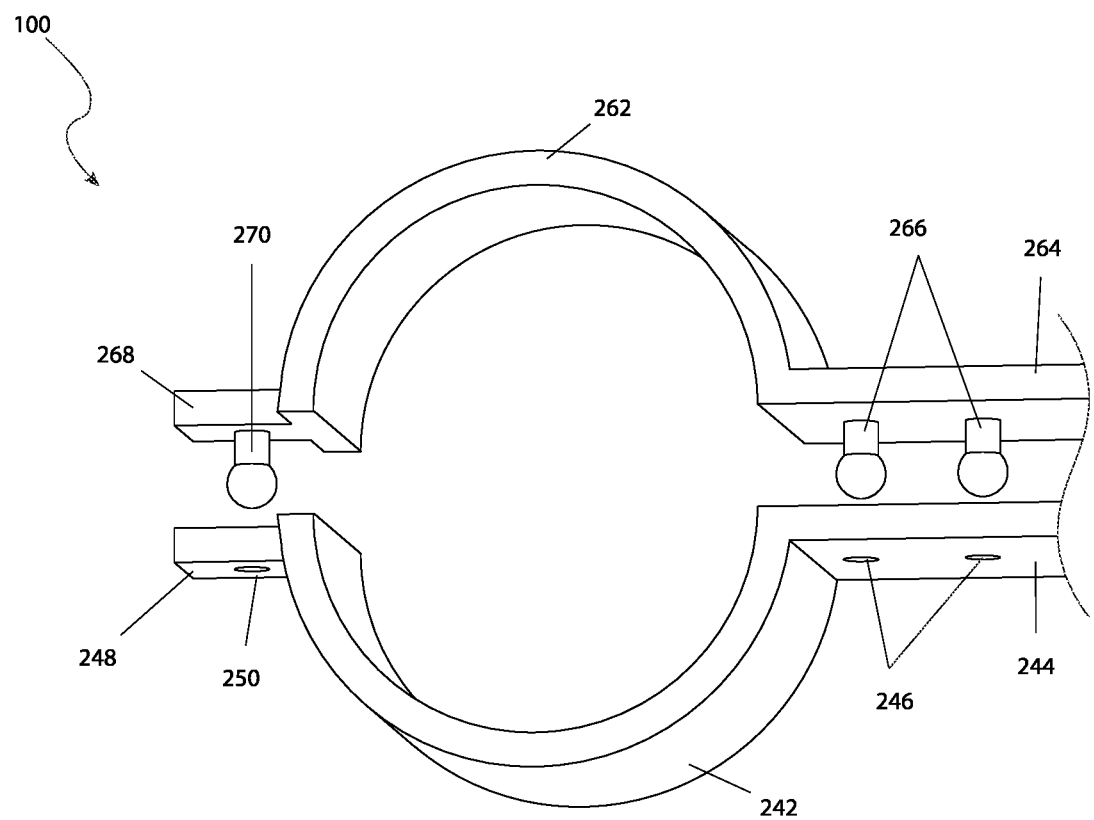
FIG. 6 is a detail view of a bed rail safety cuff, according to an embodiment of the present invention.

DESCRIPTIVE KEY 100 bed rail safety cuff
200 patient cuff 204 bed rail clamp
206 restraint
210 bottom cuff portion
212 bottom cuff shell
214 bottom cuff tab
218 bottom cuff cushion
220 strap
222 coupler
226 bottom extension arm
228 top extension arm
230 top cuff portion
232 top cuff shell
234 top cuff tab
236 strap retainer
238 top cuff cushion
240 bottom clamp portion
242 bottom clamp shell
244 bottom clamp inside tab
246 inside ball socket
248 bottom clamp outside tab
250 outside ball socket
254 bottom tension stop
256 top tension stop
258 sliding tensioner
260 top clamp portion
262 top clamp shell
264 top clamp inside tab
266 inside ball stud
268 top clamp outside tab
270 outside ball stud
272 first side grip
274 second side grip
276 bottom tensioner slot
280 top tensioner slot
282 pivot
284 coupling ring
286 break

1. DESCRIPTION OF THE INVENTION

The present invention is directed to a bed rail safety cuff (herein described as the "invention") 100. The invention 100 may comprise a patient cuff 200, a bed rail clamp 204, and a restraint 206. The invention 100 may be adapted to safely restrain movement of a patient's extremity by coupling the patient's extremity to a bed rail of a hospital bed. As non-limiting examples, restraining a patient may be necessary to prevent the patient from leaving the hospital bed, from pulling out intravenous medication lines, or from damaging medical devices when incoherent. The patient cuff 200 may be adapted to couple to the patient and the bed rail clamp 204 may be coupled to the bed rail. The patient cuff 200 may be coupled to the bed rail clamp 204 by the restraint 206 and the restraint 206 may determine the range of motion possible while restrained. More than one (1) of the safety cuffs may be used to restrain multiple extremities.

The patient cuff 200 may comprise a bottom cuff portion 210 and a top cuff portion 230. The patient cuff 200 may be adapted to removably couple to the patient's extremity with the bottom cuff portion 210 and the top cuff portion 230 on opposing sides of the patient's extremity.

The bottom cuff portion 210 may comprise a bottom cuff shell 212, a bottom cuff cushion 218, and a strap 220. The bottom cuff shell 212 may be a rigid semi-circular armature adapted to be positioned below the patient's extremity. The bottom cuff cushion 218 may be coupled to the inside surface of the bottom cuff shell 212 and may be adapted to cushion the bottom cuff shell 212 between the bottom cuff shell 212 and the patient's extremity for comfort and safety. A bottom cuff tab 214 may be a projection from the bottom cuff shell 212 oriented at a right angle to the bottom cuff shell 212. The bottom cuff tab 214 may connect the bottom cuff portion 210 to the restraint 206. The strap 220 may be a strip of flexible or semi-rigid material that may be coupled to the distal end of the bottom cuff shell 212. The strap 220 may comprise a hook-and-loop coupler 222 on one (1) side of the strap 220 such that the strap 220 may fold and couple back upon the strap 220 after passing through a strap retainer 236 located on the top cuff portion 230.

The top cuff portion 230 may comprise a top cuff shell 232 and a top cuff cushion 238. The top cuff shell 232 may be a rigid semi-circular armature adapted to be positioned above the patient's extremity. The top cuff cushion 238 may be coupled to the inside surface of the top cuff shell 232 and may be adapted to cushion the top cuff shell 232 between the top cuff shell 232 and the patient's extremity for comfort and safety. A top cuff tab 234 may be a projection from the top cuff shell 232 oriented at a right angle to the top cuff shell 232. The top cuff tab 234 may connect the top cuff portion 230 to the restraint 206. The strap retainer 236 may retain the strap 220 by creating a conduit that the strap 220 may pass through. To retain the patient cuff 200 on the patient's extremity, the strap 220 may pass through the strap retainer 236 and the strap 220 may fold back upon the strap 220. The strap 220 may then couple back upon the strap 220 such that the strap 220 creates a loop that passes through the strap retainer 236.

The bed rail clamp 204 may comprise a bottom clamp portion 240 and a top clamp portion 260. The bed rail clamp 204 may be adapted to removably couple to the bed rail with the bottom clamp portion 240 and the top clamp portion 260 on opposing sides of the bed rail.

The bottom clamp portion 240 may comprise a bottom clamp shell 242. The bottom clamp shell 242 may be a rigid semi-circular armature adapted to be positioned below the bed rail. A bottom clamp inside tab 244 may be a projection from the bottom clamp shell 242 oriented at a right angle to the bottom clamp shell 242 and directed towards the patient cuff 200. A bottom clamp outside tab 248 may be a projection from the bottom clamp shell 242 oriented at a right angle to the bottom clamp shell 242 and directed away from the patient cuff 200. The bottom clamp outside tab 248 and the bottom clamp inside tab 244 may project in opposite directions from the bottom clamp shell 242. The bottom clamp inside tab 244 may connect the bottom clamp portion 240 to the restraint 206.

The bottom clamp outside tab 248 may comprise one (1) or more outside ball sockets 250. The bottom clamp inside tab 244 may comprise one (1) or more inside ball sockets 246. The one (1) or more outside ball sockets 250 and the one (1) or more inside ball sockets 246 may be apertures for coupling the top cuff shell 232 to the bottom cuff shell 212.

The top clamp portion 260 may comprise a top clamp shell 262. The top clamp shell 262 may be a rigid semi-circular armature adapted to be positioned above the bed rail. A top clamp inside tab 264 may be a projection from the top clamp shell 262 oriented at a right angle to the top clamp shell 262 and directed towards the patient cuff 200. A top clamp outside tab 268 may be a projection from the top clamp shell 262 oriented at a right angle to the top clamp shell 262 and directed away from the patient cuff 200. The top clamp outside tab 268 and the top clamp inside tab 264 may project in opposite directions from the top clamp shell 262. The top clamp inside tab 264 may connect the top clamp portion 260 to the restraint 206.

The top clamp outside tab 268 may comprise one (1) or more outside ball studs 270. The top clamp inside tab 264 may comprise one (1) or more inside ball studs 266. The one (1) or more outside ball studs 270 and the one (1) or more inside ball studs 266 may be coupling pins for coupling the top cuff shell 232 to the bottom cuff shell 212.

The top clamp portion 260 and the bottom clamp portion 240 may couple to the bed rail by placing the top clamp portion 260 and the bottom clamp portion 240 on opposing sides of the bed rail and pressing the top clamp portion 260 and the bottom clamp portion 240 together such that the one (1) or more inside ball studs 266 on the top clamp inside tab 264 engage the one (1) or more inside ball sockets 246 on the bottom clamp inside tab 244 and the one (1) or more outside ball studs 270 on the top clamp outside tab 268 engage the one (1) or more outside ball sockets 250 on the bottom clamp outside tab 248.

In some embodiments, the restraint 206 may comprise an extension arm and a lock-in-place tensioner. The extension arm may be between five and one-half and seven and one-half inches (5½-7½ in.) long. The extension arm may comprise a bottom extension arm 226 and a top extension arm 228. The bottom extension arm 226 may couple to the bottom cuff tab 214 on the patient cuff 200 and to the bottom clamp inside tab 244 on the bed rail clamp 204. The top extension arm 228 may couple to the top cuff tab 234 on the patient cuff 200 and to the top clamp inside tab 264 on the bed rail clamp 204. The lock-in-place tensioner may comprise a sliding tensioner 258 and a plurality of tension stops. The extension arm may pass through the center of the sliding tensioner 258 with the patient cuff 200 on one (1) side of the sliding tensioner 258 and the bed rail clamp 204 on the opposite side of the sliding tensioner 258.

The sliding tensioner 258 may slide on the extension arm to tighten and loosen the patient cuff 200. The sliding tensioner 258 may stop at the plurality of tension stops situated along the extension arm. The plurality of tension stops may hold the sliding tensioner 258 in position until the sliding tensioner 258 is forced to move.

The bottom extension arm 226 may comprise a plurality of bottom tension stops 254 and the top extension arm 228 may comprise a plurality of top tension stops 256. The plurality of bottom tension stops 254 and the plurality of top tension stops 256 may be prominences that project outward from the center of the extension arm. The plurality of bottom tension stops 254 may be located opposite the plurality of top tension stops 256 such that one (1) of the plurality of bottom tension stops 254 and a corresponding one (1) of the plurality of top tension stops 256 may comprise an individual tension stop.

The sliding tensioner 258 may be a slider that encircles the extension arm. The sliding tensioner 258 may comprise a first side grip 272 and a second side grip 274 on opposing lateral side of the sliding tensioner 258. The first side grip 272 and the second side grip 274 may be adapted for a caregiver to grasp while sliding the sliding tensioner 258. The sliding tensioner 258 may further comprise a bottom tensioner slot 276 on the bottom surface of the sliding tensioner 258 and a top tensioner slot 280 on the top surface of the sliding tensioner 258. The bottom tensioner slot 276 may engage one (1) of the plurality of bottom tension stops 254 and the top tensioner slot 280 may engage one (1) of the plurality of top tension stops 256 to hold the sliding tensioner 258 in place when the bottom tensioner slot 276, one (1) of the plurality of bottom tension stops 254, the top tensioner slot 280, and one (1) of the plurality of top tension stops 256 align. The sliding tensioner 258 may be adapted to disengage the bottom tensioner slot 276 from the plurality of bottom tension stops 254 and to disengage the top tensioner slot 280 from the plurality of top tension stops 256 when the caregiver squeezes the sliding tensioner 258 between the first side grip 272 and the second side grip 274, causing the top and bottom surface of the sliding tensioner 258 to flex away from the extension arm.

In some embodiments, the restraint 206 may comprise a pivot 282 that may couple the bottom cuff tab 214, the top cuff tab 234, the bottom clamp inside tab 244, and the top clamp inside tab 264. The pivot 282 may enable the pivoting of the top cuff tab 234 relative to the bottom cuff tab 214 such that the top cuff portion 230 may separate from the bottom cuff portion 210 when the strap 220 is decoupled. The pivot 282 may enable the pivoting of the top clamp inside tab 264 relative to the bottom clamp inside tab 244 such that the top clamp portion 260 may separate from the bottom clamp portion 240 when the top clamp portion 260 is decoupled from the bottom clamp portion 240.

In some embodiments, the restraint 206 may comprise a coupling ring 284. The coupling ring 284 may be inserted at a break 286 in the bottom cuff tab 214 and the top cuff tab 234 such that the coupling ring 284 may introduce at least one (1) additional degree of freedom to the motion of the patient cuff 200.

The safety cuffs 100 may be adapted to more fully restrain the patient by using multiples of the safety cuffs simultaneously. As a non-limiting example, two (2) safety cuffs 100 may be adapted to restrain both arms, both legs, or an arm and a leg on the same side of the patient. As a further non-limiting example, four (4) safety cuffs 100 may be adapted to restrain both arms and both legs at the same time.

In use, a patient may be restrained in a hospital bed by coupling the bed rail clamp 204 to a bed rail and by coupling the patient cuff 200 to a patient's extremity. The bed rail clamp 204 may be coupled to the bed rail by placing the top clamp portion 260 and the bottom clamp portion 240 on opposites sides of the bed rail and pressing them together such that the one (1) or more inside ball studs 266 engage the one (1) or more inside ball sockets 246 and the one (1) or more outside ball studs 270 engage the one (1) or more outside ball sockets 250. The patient cuff 200 may be coupled to the patient's extremity by placing the top cuff portion 230 and the bottom cuff portion 210 on opposites sides of the patient's extremity, feeding the strap 220 through the strap retainer 236, folding the strap 220 back on itself, and fixing the strap 220 in place using the coupler 222. In some embodiments, the patient cuff 200 may be adjusted using the lock-in-place tensioner to tighten or loosen the patient cuff 200 by sliding the sliding tensioner 258 towards or away from the patient cuff 200 until the sliding tensioner 258 engages one or the plurality of tension stops.

To remove the safety cuff 100, the coupler 222 may be decoupled and the strap 220 may be removed from the strap retainer 236 and the top clamp portion 260 and the bottom clamp portion 240 may be pulled apart.

Two (2) safety cuffs 100 or four (4) safety cuffs 100 may be used to more securely restrain the patient.

The exact specifications, materials used, and method of use of the invention 100 may vary upon manufacturing. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A bed rail safety cuff, comprising:
   a patient cuff having a bottom cuff portion and a top cuff portion, the patient cuff is adapted to couple to a patient's extremity with the bottom cuff portion and the top cuff portion on opposing sides of the patient's extremity, and the bottom cuff portion includes a bottom cuff shell, a bottom cuff cushion, and a strap;
   a bed rail clamp includes a bottom clamp portion and a top clamp portion, the bed rail clamp is adapted to removably couple to the bed rail with the bottom clamp portion and the top clamp portion on opposing sides of the bed rail; and
   a restraint having an extension arm and a lock-in-place tensioner, the restraint couples the patient cuff to the bed rail clamp to determine a range of motion possible while the patient is restrained and
   wherein the bottom clamp portion includes a bottom clamp shell that is a rigid semi-circular armature adapted to be positioned below the bed rail;
   wherein a bottom clamp inside tab is a projection from the bottom clamp shell oriented at a right angle to the bottom clamp shell and directed towards the patient cuff;
   wherein a bottom clamp outside tab is a projection from the bottom clamp shell oriented at a right angle to the bottom clamp shell and directed away from the patient cuff;
   wherein the bottom clamp outside tab and the bottom clamp inside tab project in opposite directions from the bottom clamp shell and the bottom clamp inside tab connect the bottom clamp portion to the restraint; and
   wherein the bottom clamp outside tab includes one or more outside ball sockets and the bottom clamp inside tab includes one or more inside ball sockets that are a plurality of apertures for coupling the top cuff shell to the bottom cuff shell.

2. The bed rail safety cuff, according to claim 1, wherein the bottom cuff cushion is coupled to an inside surface of the bottom cuff shell and is adapted to cushion the bottom cuff shell between the bottom cuff shell and the patient's extremity for comfort and safety.

3. The bed rail safety cuff, according to claim 1, further comprising a bottom cuff tab is a projection from the bottom cuff shell oriented at a right angle to the bottom cuff shell and the bottom cuff tab connects the bottom cuff portion to the restraint.

4. The bed rail safety cuff, according to claim 1, wherein the strap includes a hook-and-loop coupler one side of the strap such that the strap folds and couples back upon the strap after passing through a strap retainer located on the top cuff portion.

5. The bed rail safety cuff, according to claim 4, wherein to retain the patient cuff on the patient's extremity, the strap passes through the strap retainer and the strap folds back upon the strap.

6. The bed rail safety cuff, according to claim 5, wherein the strap couples back upon the strap such that the strap creates a loop that passes through the strap retainer.

7. The bed rail safety cuff, according to claim 1, wherein a top cuff cushion is coupled to an inside surface of a top cuff shell and is adapted to cushion the top cuff shell between the top cuff shell and the patient's extremity for comfort and safety.

8. The bed rail safety cuff, according to claim 1, wherein a top cuff tab is a projection from the top cuff shell oriented at a right angle to the top cuff shell.

9. The bed rail safety cuff, according to claim 1, wherein the top clamp portion includes a top clamp shell adapted to be positioned above the bed rail.

10. The bed rail safety cuff, according to claim 9, wherein a top clamp inside tab is a projection from the top clamp shell oriented at a right angle to the top clamp shell and directed towards the patient cuff.

11. The bed rail safety cuff, according to claim 9, wherein a top clamp outside tab is a projection from the top clamp shell oriented at a right angle to the top clamp shell and directed away from the patient cuff.

12. The bed rail safety cuff, according to claim 11, wherein the top clamp outside tab and the top clamp inside tab project in opposite directions from the top clamp shell.

13. The bed rail safety cuff, according to claim 1, wherein the top clamp outside tab includes one or more outside ball studs.

14. The bed rail safety cuff, according to claim 13, wherein the one or more outside ball studs and the one or more inside ball studs are a plurality of coupling pins for coupling the top clamp shell to the bottom clamp shell.

15. The bed rail safety cuff, according to claim 1, wherein the top clamp portion and the bottom clamp portion couple to the bed rail by placing the top clamp portion and the bottom clamp portion on opposing sides of the bed rail and pressing the top clamp portion and the bottom clamp portion together such that the one or more inside ball studs on the top clamp inside tab engage the one or more inside ball sockets on the bottom clamp inside tab and the one or more outside ball studs on the top clamp outside tab engage the one or more outside ball sockets on the bottom clamp outside tab.

* * * * *